United States Patent
Coppolino et al.

(10) Patent No.: US 7,517,868 B2
(45) Date of Patent: *Apr. 14, 2009

(54) PHYTIC CITRATE COMPOUNDS AND PROCESS FOR PREPARING THE SAME

(75) Inventors: Carl A. Coppolino, Alpharreta, GA (US); AbulKalam M. Shamsuddin, Lutherville, MD (US)

(73) Assignee: IP-6 Research Inc, Baltimore, MD (US)

( * ) Notice: Subject to any disclaimer, the term of this patent is extended or adjusted under 35 U.S.C. 154(b) by 396 days.

This patent is subject to a terminal disclaimer.

(21) Appl. No.: 11/320,834

(22) Filed: Dec. 30, 2005

(65) Prior Publication Data

US 2006/0106001 A1      May 18, 2006

Related U.S. Application Data

(63) Continuation-in-part of application No. 10/894,919, filed on Jul. 19, 2004, now Pat. No. 7,009,067.

(51) Int. Cl.
*A61K 31/661* (2006.01)
*C07F 9/06* (2006.01)

(52) U.S. Cl. .................... 514/102; 558/70; 558/155

(58) Field of Classification Search .......... 558/70, 558/87, 129, 155; 514/102
See application file for complete search history.

(56) References Cited

U.S. PATENT DOCUMENTS 5,114,974 A    5/1992   Rubin
6,114,387 A    9/2000   Cutler
7,009,067 B2 *  3/2006  Coppolino ............... 558/70

* cited by examiner

*Primary Examiner*—Golam M Shameem
(74) *Attorney, Agent, or Firm*—Bingham McCutchen LLP

(57) ABSTRACT

The present invention provides a chemical compound or a salt thereof having the chemical formula of:

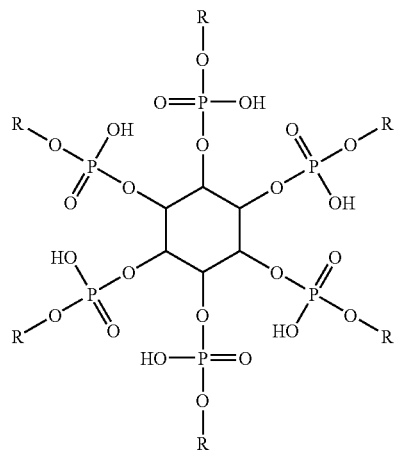

wherein said R is H or citrate and wherein at least one R is citrate. The salt of the chemical compound is the $Na^+$, $K^+$, $Mg^{2+}$, or $Ca^{2+}$ salt of said chemical compound. The chemical compound is a chelator which chelates sodium, potassium or lithium, magnesium, calcium, copper, iron, lead, zinc, aluminum, mercury, cadmium, or chromium. It is also be used as an artery plaque dissolver and/or to treat age-related degenerative disorders, such as Alzheimer's disease. The present invention also provides a method for producing the phytic citrate compound and/or its salt.

18 Claims, 2 Drawing Sheets

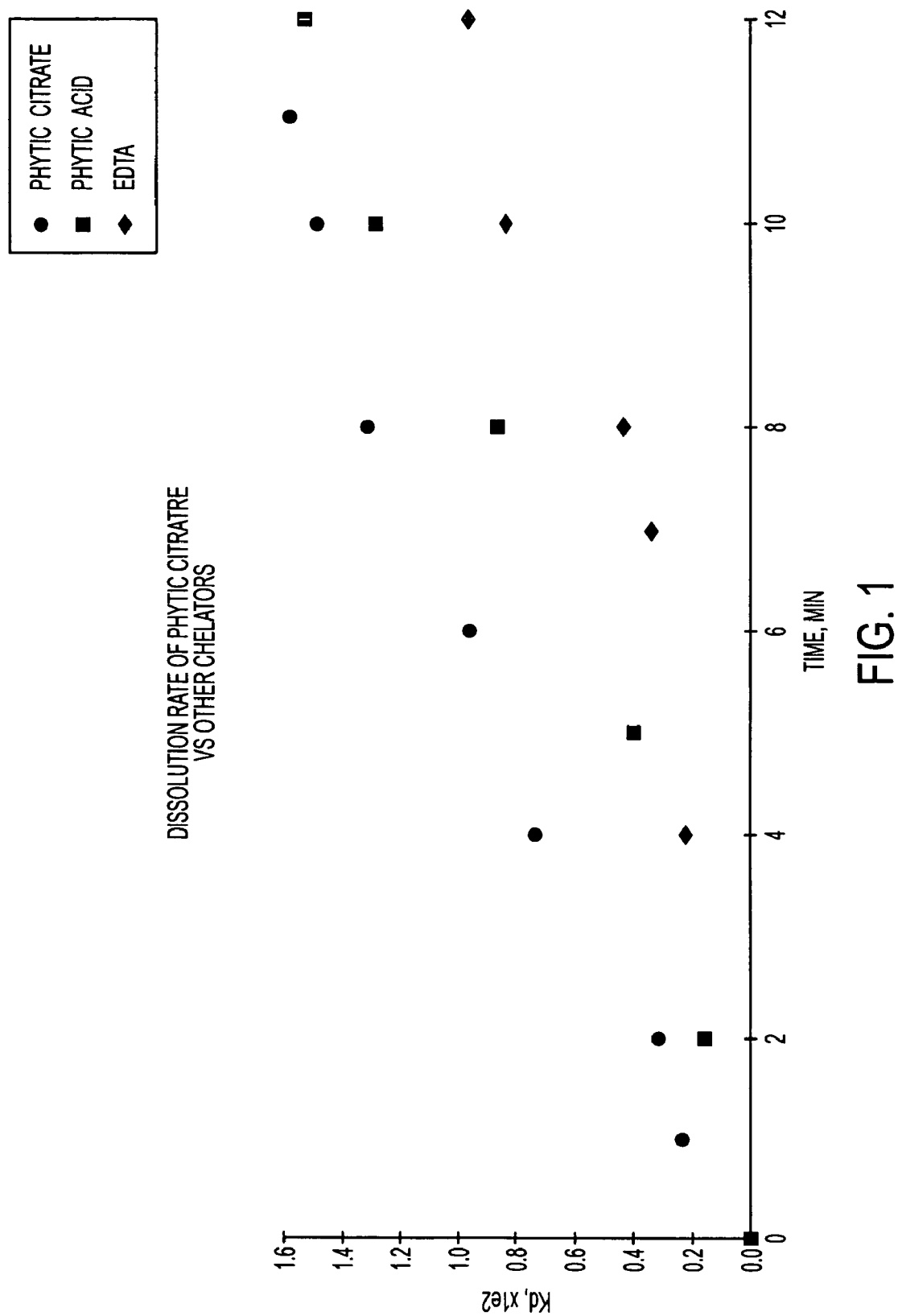

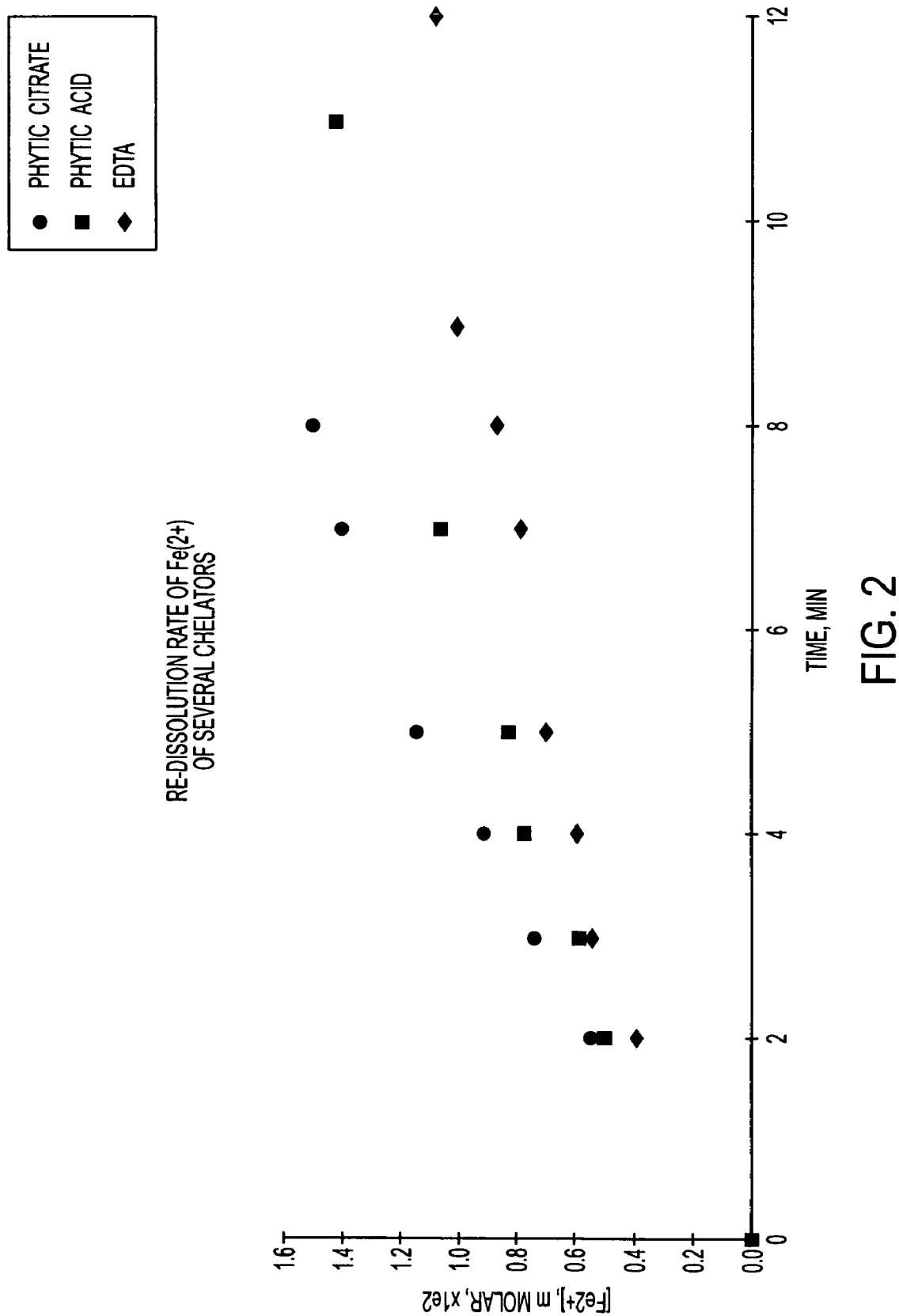

PHYTIC CITRATE COMPOUNDS AND PROCESS FOR PREPARING THE SAME

RELATED APPLICATION

This is a continuation-in-part application which claims the priority of U.S. patent application Ser. No. 10/894,919, filed on Jul. 19, 2004 now U.S. Pat. No. 7,009,067, which is incorporated herein by reference.

FIELD OF THE INVENTION

The present invention relates to a group of chemical compounds (hereinafter "phytic citrate compounds") and/or their salts thereof having the chemical formula of:

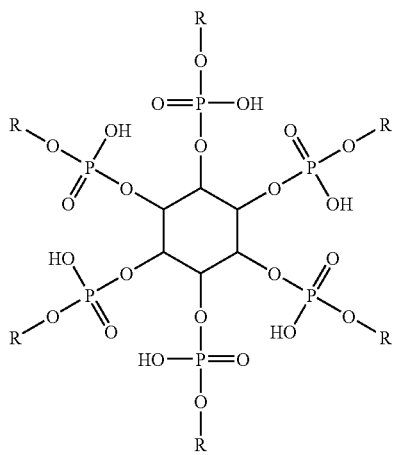

wherein R is H or citrate and wherein at least one R is a citrate. The salts of the phytic citrate compounds include the $Na^+$, $K^+$, $Mg^{2+}$, and/or $Ca^{2+}$ salts of the phytic citrate compounds. The phytic citrate compounds are excellent metal chelators which chelate sodium, potassium or lithium, magnesium, calcium, copper, iron, lead, zinc, aluminum, mercury, cadmium, or chromium efficiently. They are also good artery plaque dissolvers and can be used to treat age-related degenerative disorders, such as Alzheimer's disease. The present invention also provides a method for producing the phytic citrate compounds and/or their salts.

BACKGROUND OF THE INVENTION

Chelators are small molecules that bind very tightly to metal ions. Some chelators are simple molecules that are easily manufactured (e.g., ethylenediaminetetraacetic acid [EDTA]). Others are complex proteins made by living organisms (e.g., transferrin). The key property shared by all chelators is that the metal ion bound to the chelator is chemically inert. Consequently, one of the important roles of chelators is to detoxify metal ions and prevent poisoning. For instance, ethylendiaminetetraacetic acid (EDTA) is used to treat patients with extreme, life-threatening hypercalcaemia, while the iron chelator, desferrioxamine, is used to remove excess iron that accumulates with chronic blood transfusions. Although many different types of chelators exist, only a few are clinically useful since most have dangerous side effects. EDTA has long been thought of as a significant chelating agent. However, there has been known toxicological implications of EDTA when significant quantities and concentrations enter the vascular system. (See U.S. Pat. Nos. 5,114,974 and 6,114,387).

Meanwhile, phytic acid in the medical community has been known as an alternative to EDTA as a chelating agent. Phytic acid is a component of every plant seed and is found in a number of cereals and seeds. Although it is very soluble in water, alcohol (95% by volume) and acetone, it is only relatively soluble in aqueous propylene glycol and aqueous glycerol, and practically insoluble in ether, benzene and hexane. Aqueous solutions of phytic acid are intensely acidic: pH 0.9 at 66 grams/liter. Although phytic acid is a stable bioactive ingredient and free radical inhibitor with metal chelation abilities with strong buffering and anti-oxidant properties, it cannot be utilized as a proprietary flagship product.

In the invention to be presented below, a group of novel chemical compounds (hereinafter "phytic citrate compounds") will be introduced. These novel compounds have at least one citrate molecule attached at the hydroxyl group of the citric acid to the phosphate of the phytate molecule. The novel compounds demonstrate superior chelating effect than EDTA and have the advantages to be used in humans due to their biodegradable and non-toxic properties.

SUMMARY OF THE INVENTION

The present invention provides a group of novel chemical compounds ("phytic citrate compounds") and/or their respective salts. These novel chemical compounds are represented by the following formula:

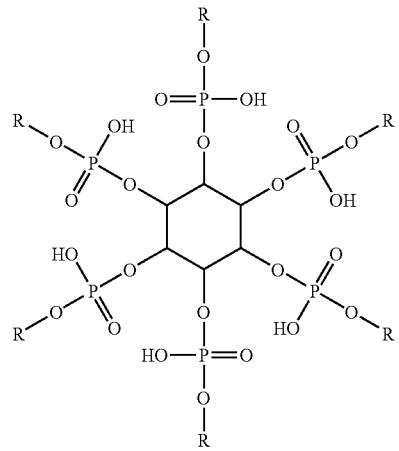

wherein R is H, or citrate; and wherein at least one R is citrate. Thus, the above identified compounds include phytic mono-citrate, phytic di-citrate, phytic tri-citrate, phytic tetra-citrate, phytic penta-citrate, and phytic hexa-citrate. The most preferable compound is phytic hexa-citrate. The salts of the respective phytic citrate compounds include $Na^+$, $K^+$, $Mg^{2+}$, or $Ca^{2+}$ salts of the compounds. The most favorable salts are the $Ca^{2+}$, $Mg^{2+}$, and $Ca^{2+}$ $Mg^{2+}$ salts of the compounds.

The phytic citrate compounds are each in a crystalline form, preferably in a crystalline powder form. Additionally, the phytic citrate compounds are soluable in aqueous solution, preferably in water solution.

The phytic citrate compounds are effective metal chelators, which are capable of chelating mono-, bi-, and tri-valent ions, such as sodium, potassium or lithium, magnesium, calcium, copper, iron, lead, zinc, aluminum, mercury, cadmium, and/or chromium.

The phytic citrate compounds also have therapeutic effects on dissolving artery plaque and/or for treating age-related degenerative disease, such as Alzheimer's disease.

The present invention also provides a pharmaceutical composition which contains the phytic citrate compound or the salt thereof and a pharmaceutically acceptable carrier.

The present invention also provides a method for producing the phytic citrate compounds. The method includes the following steps: (1) dissolving a salt of phytic acid in an aqueous solution; (2) adding and stirring citric acid and/or citrate to the dissolved salt of phytic acid to form a citrated phytate solution; and (3) crystallizing the citrated phytate solution to form the phytic citrate compound and/or the salt thereof.

Based on the various quantities of Na-Phytate and citric acid/citrate used in the reaction, phytic mono-citrate, phytic di-citrate, phytic tri-citrate, phytic tetra-citrate, phytic penta-citrate, and phytic hexa-citrate is produced. For example, Na-phytate and citric acid (or citrate) in the molar ratio of about 1:1, 1:2, 1:3, 1:4, 1:5, and 1:6, respectively, could produce phytic mono-citrate, phytic di-citrate, phytic tri-citrate, phytic tetra-citrate, phytic penta-citrate, and phytic hexa-citrate, respectively.

The salt of phytic acid used in the production of the phytic citrate compound includes sodium phytate, potassium phytate, magnesium phytate, calcium phytate, and/or calcium magnesium phytate. The salt of the phytic acid is preferably dissolved in water. The dissolved citrated phytate solution is preferably to be heated, but up to less than 100° C. The phytic citrate compounds can be crystallized by any conventional drying method, preferably under 40° C., and most favorably under 10° C.

BRIEF DESCRIPTION OF THE DRAWINGS

FIG. 1 shows the dissolution rate of the phytic citrate compound (phytic hexa-citrate) of the present invention (●), as compared to those of phytic acid (■), and EDTA (♦). The results demonstrate that phytic citrate exhibits superior dissolution capability to phytic acid and EDTA.

FIG. 2 shows the Re-dissolution rate of $Fe^{2+}$ of the phytic citrate compound (phytic hexa-citrate) of the present invention (●), as compared to those of phytic acid (■), and EDTA (♦). The results demonstrate that phytic citrate exhibits superior redissolution capability to phytic acid and EDTA.

DETAILED DESCRIPTION OF THE INVENTION

The present invention provides a group of new chemical compounds known as the phytic citrate compounds and/or the salts of these compounds. The present invention also provides a method for producing these compounds and/or their salts. The phytic citrate compounds attach one to six molecules of citrate to a single phytate molecule by converting the three carboxyl branches of the citric acid into three hydroxyl groups, thus, making the new compounds water soluble, due to the existence of the hydrophilic hydroxyl groups.

In the phytic citrate compounds, citric acid has been converted to a citrate with three hydroxyl groups per molecule. Each of the six carbons of the citrate has an oxygen atom bound to the citrate molecule and the three hydroxyl groups are connected to each carbon atom of the citrate molecule. Due to the chemical structures of these new compounds, particularly the large polar molecule with numerous hydroxyl groups, these compounds possess high solubility and chelation properties. These new phytic citrate compounds have one to six citrate molecules attached at the hydroxyl group of the citric acid to the phosphates of the phytate molecule. The resulting phytic citrate compounds have the following generic formula:

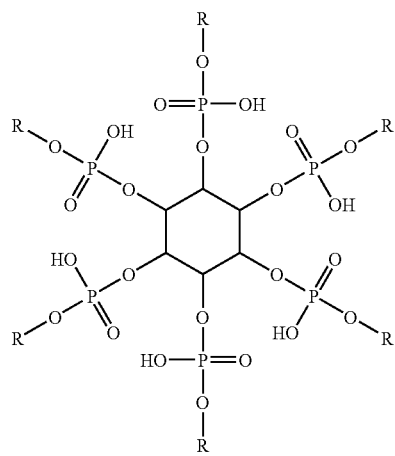

where R is H or citrate and where at least one R is citrate.

The following examples illustrate the methods for making the phytic citrate compounds and the characteristics of the phytic citrate compounds. These examples, however, are for illustrative purposes. They should not be viewed as limitations of the scope of the present invention. Reasonable variations, such as those that occur to a reasonable artisan, can be made herein without departing from the scope of the present invention.

EXAMPLE 1

Method for Preparation of the Phytic Citrate Compounds

Sodium Phytate was available commercially. The phytic citrate compounds were made by dissolving sodium phytate in water. If necessary, heat and reflux could be used to facilitate the dissolution of sodium phytate. It was preferred that the heating of the solution was controlled to no more than 100° C. and no more than 30 minutes. An adequate amount of citric acid or sodium citrate was then added to the dissolved phytate solution. The mixture was thoroughly stirred and then was sat for no more than 40° C., preferably in refrigerating environment (i.e., about 4-10° C.), for approximately 6-8 hours to allow the newly formed phytic citrate compounds to crystallize or until the crystallization ceased. The phytic citrate compounds were dried under room temperature by any conventional methods, including, but not limited to, vaccum drying, freeze-drying, or drying at room temperature. Based on the quantities of the citric acid/citrate added, phytic mono-citrate, phytic di-citrate, phytic tri-citrate, phytic tetra-citrate, phytic penta-citrate, and phytic hexa-citrate, were produced. For example, Na-phytate and citric acid (or citrate) in the molar ratio of about 1:1, 1:2, 1:3, 1:4, 1:5, and 1:6, respectively, could produce phytic mono-citrate, phytic di-citrate, phytic tri-citrate, phytic tetra-citrate, phytic penta-citrate, and phytic hexa-citrate, respectively.

EXAMPLE 2

Method for Preparation of Phytic Hexa-Citrate

Alternatively, the phytic hexa-citrate compound was produced by the following method: First, 0.33 kg of calcium carbonate was slowly added, in increments of 0.1 kg, to 0.87 kg of phytic acid liquid. The mixture was heated and refluxed for about one hour at about 90° C. The two solids were separated and filtered. The white solid, which was calcium phytate, was collected. About 1 kg of the calcium phytate was dissolved into 2.0 liters of water and heated to about 89° C. for about 10-15 minutes until calcium phytate was completely dissolved in the water solution. About 0.9 kg of citric acid was then added to and stirred in the calcium phytate soluttion until the citric acid was completely dissolved. The heat source was removed and the resulting mixture was left sat at no more than 40° C. or in a refrigerated environment at a temperature of about 5-10° C. to allow the newly formed phytic hexa-citrate to crystallize for approximately 6 to 8 hours or until crystallization has ceased. The mixture was allowed to dry out at room temperature until no liquid was visible. The crystals were spread in a drying pan for approximately 24 hours at a temperature of no more than 40° C., which yielded approximately 1.2 kg of hexa-citrated phytate.

EXAMPLE 3

Chelating Effects of the Phytic Citrate Compounds

As shown below in Table 1 and in FIGS. 1-2, the phytic citrate compounds were very effective oral chelators, which could maintain metals and metalloids in the saline solution of blood. The new chemical compounds were also very effective in dissolving artery plaque, as well as removing excess copper, zinc, aluminum and iron in brain tissue, thus, providing a therapeutic means to treat patients with Alzheimer's disease, which is known to be caused by accumulation of metals in the patients' brain tissues.

Chelation is a term which refers to the maintenance of soluble (dissolved) state of an ion, atom, or molecule. A chelator is an additive which can redissolve a solid material which has been suspended or has settled in a solution as a solid (precipitate). A strong chelator has the ability not only to dissolve the solid precipitates but also to powerfully maintain the dissolved state of particular solids. Chelators are used in industrial applications to prevent heavy metal from precipitating or falling out from solutions. There are many industrial chelators available commercially for various applications of water treatment or to maintain ingredients of a solution to stay dissolved indefinitely. The mechanism by which a chelator maintains the solubility of what would otherwise be a solid is as follows: the chelator surrounds the atom, ion or molecule which normally cannot dissolve in water. The chelator then attaches to the solid at its hydrophobic end. The chelator molecules then, once completely surrounding the solid, now create an exterior shell of the hydrophilic end of the chelator enabling the solid molecule to dissolve completely in the solution even where it before would have existed as a precipitated solid.

Phytic acid is a very strong chelator of bivalent and trivalent heavy metals such as mercury, cadmium, chromium, iron, lead and aluminum. Citric acid on the other hand is a very effective chelator for a monovalent ion, such as sodium, potassium and lithium. After consideration of many different nutritional supplements and bulk food commodities, it was discovered after countless experiments and computer modeling that the molecular structure of citric acid could be combined with phytic acid to form the new compounds possessing most of the beneficial qualities of phytic acid and citric acid, which have been named the phytic citrate compounds. These include phytic mono-citrate, phytic di-citrate, phytic tri-citrate, phytic tetra-citrate, phytic penta-citrate, and/or phytic hexa-citrate. Among these compounds, hexa-citrated phytate has the best chelating effect. The superior chelating effect of hexa-citrated phytate, as opposed to other known chelators, such as EDTA, acetic acid, lactic acid, citric acid, gluconic acid, and polyphosphoric acid, is demonstrated in the following Table:

TABLE 1

| | COMPARISON OF CHELATING EFFECTS | | | | |
|---|---|---|---|---|---|
| | $Mg^{2+}$ | $Ca^{2+}$ | $Cu^{2+}$ | $Fe^{2+}$ | $Zn^{2+}$ |
| | (conc. of ions chelated) | | | | |
| Phytic citrate | 11.56 | 12.24 | 12.11 | 20.44 | 21.01 |
| Phytic acid (pH 3) | 9.56 | 9.73 | 10.41 | 16.84 | 15.50 |
| Phytic acid (pH 5) | 10.77 | 10.55 | 10.85 | 17.35 | 14.96 |
| Phytic acid (pH 7) | 11.24 | 10.57 | | | |
| EDTA | 8.69 | 10.70 | 18.80 | 17.35 | 16.50 |
| Acetic acid | 0.51 | 0.53 | | | 1.03 |
| Lactic acid | 0.93 | 1.07 | 3.02 | 6.40 | 1.86 |
| Citric acid | 2.80 | 3.50 | 6.10 | 11.85 | 4.50 |
| Gluconic acid | 0.70 | 1.20 | | | 1.70 |
| Polyphosphoric acid | 3.20 | 3.0 | 3.5 | | 2.00 |

The chelating effects of the various chelators were measured by the conventional method known to an artisan in the art. The concentration of the ions chelated by the chelator was determined using a divalent cation electrode (e.g., Model 93-32, made by Orion Research Incorporated) and an ion analyzer (e.g., Model EA 920, made by Orion Research Incorporated).

The results of Table 1 demonstrate that phytic citrate has superior chelating effects to other chelators.

FIG. 1 shows the dissolution rate (Kd) of phytic citrate (FIG. 1), as compared to those of phytic acid and EDTA. The results demonstrate that phytic acid has superior dissolution capability to other chelators in dissolving plaques in the artery.

FIG. 2 shows the re-dissolution rate of $Fe^{2+}$ (in brain tissues) among phytic citrate, phytic acid and EDTA. The superior ability of phytic tissue to redissolve iron ion in the brain tissue provides a way to treat age-related degenerative disease, such as Alzheimer's disease.

EXAMPLE 4

Crystalline Property of the Phytic Citrate Compounds

Table 2 shows the crystalline property of phytic citrate, as opposed to phytic acid, calcium phytate, and calcium magnesium phytate:

TABLE 2

PROPERTIES OF PHYTIC CITRATE, PHYTIC ACID, Ca PHYTATE, Ca Mg PHYTATE, AND Na PHYTATE

|  | Phytic Citrate | Phytic Acid | Ca-Phytate | CaMg-Phytate |
|---|---|---|---|---|
| Appearance | White crystalline powder | Slight yellow viscous liquid | white powder | white powder |
| Solubility | Very soluble in water | N/A | Easily soluble in acid but insoluble in water | Very soluble in acid but insoluble in water |
| Heavy metals (as Pb) | max 0.0013% | max 0.0025% | max 0.005% | max 0.005% |
| Arsenic | max 0.0002% | max 0.0003% | max 0.0005% | max. 0.0005% |
| sulfate | max. 0.007% | max. 0.071% | ND* | ND* |

ND*: Not determined

The results as shown in Table 2 demonstrate that phytic citrate (phytic hexa-citrate) was in crystalline form. It was extremely soluble in water, and it contained very low amounts of heavy metals (lead), arsenic and sulfate. These results support the notion that phytic citrate was easy to be dissolved, and contained low toxic substances, so that it could be used safely by humans.

EXAMPLE 5

Biodegradability of Phytic Citrate

The biodegradability of phytic citrate was evaluated according to the method of "301 A DOC Die-Away Test" (1993), OECDGuidelines for Testing of Chemicals. The results from degradation at both 7 and 14 days were shown in Table 3.

TABLE 3

BIODEGRADABILITY OF PHYTIC CITRATE

| Test Flask | Degradation (%) in days | | |
|---|---|---|---|
|  | 7 | 14 | 14 (mean) |
| Test suspension | | | |
| 1 | >90 (98.0) | >90 (98.6) | |
| 2 | >90 (97.6) | >90 (100) | >90 (99.5) |
| 3 | >90 (99.4) | >90 (100) | |
| Abiotic sterile control | <10 | <10 | — |
| Absorption | <10 | <10 | — |
| Aniline Reference | >90 (100) | >90 (99.7) | — |

The results as shown in Table 3 demonstrate that phytic citrate was readily biodegradable so that it was safe to be used in humans.

CONCLUSION

The phytic citrate compound of the present invention evolves with several characteristics of both citric acid and phytic acid, which are both considered to be very beneficial additives in the diet of human beings, and non-toxic. Thus, the phytic citrate compounds not only demonstrated a superior chelating effects than EDTA (as shown in Table 1), but also were non-toxic (as shown in Table 2), and could be biodegradable (as shown in Table 3) so that it was superior to EDTA, which has shown toxic and carcinogenic characteristics.

Additionally, since citrate is combined with phytic acid at the carbon oxygen bond on each of the carbon atoms of the aromatic ring, the bonds between the oxygen atom of phytic acid and the citrate complex form very strong covalent bonds that help prevent instability of the molecule. Further, the phytic citrate compounds are very soluble despite its high molecular weight (as demonstrated in Table 2). Due to its numerous hydroxyl groups, the phytic citrate compound is an extremely polar molecule that far exceeds the solubility and chelation properties of other conventional chelators, such as inositol, phytic acid, and citric acid.

One primary use of the phytic citrate compound is to act as an artery plaque dissolver, due to its superior metals dissolution/chelation rate (as shown in FIG. 2). As many are aware, blood acts as a concentrated saline solution containing both dissolved and suspended solids that rapidly circulate through the arteries and the arterioles. Dissolved solids in the blood include nutrients absorbed from the colon and/or intestinal track. Suspended solids include platelets, red blood cells and white blood cells. Over time, some dissolved solids form solid precipitates that adhere to the inner walls of the circulatory system forming solid arterial plaque, which can lead to severe blockage in major blood vessels. However, due to the many chemical properties of the phytic citrate compound, it is particularly successful in stripping plaque from arteries and arterioles. For example, the phytic citrate compound is a highly soluble molecule with both hydrophobic and hydrophilic properties. Such a characteristic allows the phytic citrate compound to remain dissolved in water due to its hydrophilic properties, while also allowing it to attach or adhere itself to solids that it comes into contact with as a result of its hydrophobic properties. As such, the phytic citrate compound acts similarly to a surfactant allowing it to act as a removal agent of plaque from arteries and arterioles, while it rapidly flows through the cardiovascular system.

Additionally, the phytic citrate compound has very powerful chelation characteristics that re-dissolve the precipitated solids. These re-dissolved materials are maintained in their soluble form until they are eventually excreted through the renal system. As demonstrated in FIG. 2, the phytic citrate compounds were especially effective in re-dissolving iron ions in brain tissue, which could be used for treating patients with degenerative disease, such as Alzheimer's disease.

Finally, the phytic citrate compound has several novel and significant differences from the conventional chelators. First, the chemical compound has a rapid dissolution constant, which allows it to dissolve rapidly and readily. Due to this enhanced chelating capacity, the bonding of metals and metalloids with the conjugate product produces a soluble ionic product that maintains its soluble form in high concentrations in the saline solution of blood. As such, the chemical compound at very low concentrations has the ability to dissolve artery plaque for treatment of arteriosclerosis, as well as the ability to remove copper, zinc, and iron deposits in the brain tissue for treatment of Alzheimer's disease and other age-related degenerative disorders.

While the above description contains many specificities, these should not be construed as limitations on the scope of the invention, but as exemplifications of the presently preferred embodiments thereof. Many other ramifications and variations are possible within the teachings of the invention. Thus, the scope of the invention should be determined by the appended claims and their legal equivalents, and not by the examples given.

We claim:

1. A chemical compound or a salt thereof; wherein said chemical compound is represented by the following formula:

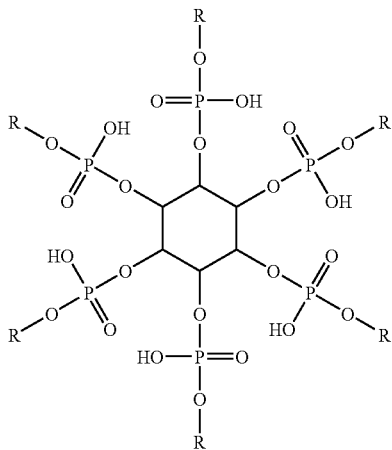

wherein R is H, or citrate; and wherein at least one R is citrate.

2. The chemical compound or the salt thereof according to claim 1, wherein said salt of said chemical compound contains an ion selected from the group consisting of $Na^+$, $K^+$, $Ca^{2+}$, and $Mg^{2+}$.

3. The chemical compound or the salt thereof according to claim 1, wherein said chemical compound is in a crystalline form.

4. The chemical compound or the salt thereof according to claim 1, wherein said chemical compound is dissolved in an aqueous solution.

5. The chemical compound or the salt thereof according to claim 4, wherein said aqueous solution is water.

6. The chemical compound or the salt thereof according to claim 1, wherein said chemical compound is a chelator.

7. The chemical compound or the salt thereof according to claim 6, wherein said chemical compound chelates sodium, potassium or lithium, magnesium, calcium, copper, iron, lead, zinc, aluminum, mercury, cadmium, or chromium.

8. The chemical compound or the salt therof according to claim 1, wherein said chemical compound or the salt thereof is an artery plaque dissolver.

9. The chemical compound or the salt thereof according to claim 1, wherein said chemical compound or the salt thereof has therapeutic effect on treating age-related degenerative disorder in a host.

10. The chemical compound or the salt thereof according to claim 9, wherein said age-related degenerative disorder is Alzheimer's disease.

11. A pharmaceutical composition comprising the chemical compound or the salt thereof according to claim 1 and a pharmaceutically acceptable carrier.

12. A method for producing the chemical compound according to claim 1 comprising: dissolving a salt of phytic acid in an aqueous solution; adding and stirring citric acid and/or citrate to said dissolved salt of phytic acid to form a citrated phytate solution; crystallizing said citrated phytate solution to form said chemical compound or the salt thereof.

13. The method according to claim 12, wherein said chemical compound is mono-citrate, phytic di-citrate, phytic tri-citrate, phytic tetra-citrate, phytic penta-citrate, or phytic hexa-citrate.

14. The method according to claim 12, wherein said phytate mono-citrate, said phytic di-citrate, said phytic tri-citrate, said phytic tetra-citrate, said phytic penta-citrate, or said phytic hexa-citrate, respectively, is produced when the salt of phytic acid and citric acid/citrate is in a molar ratio of about 1:1, 1:2, 1:3, 1:4, 1:5, or 1:6, respectively.

15. The method according to claim 12, wherein said salt of phytic acid is sodium phytate, potessium phytate, magnesium phytate, calcium phytate, or calcium magnesium phytate.

16. The method according to claim 12, wherein said aqueous solution is water.

17. The method according to claim 12, wherein said citrated phytate is formed with heat.

18. The method according to claim 12, wherein said chemical compound or the salt thereof is crystallized by drying.

* * * * *